United States Patent [19]

Heimer

[11] Patent Number: 5,185,245
[45] Date of Patent: Feb. 9, 1993

[54] IMMUMOASSAYS AND KIT FOR DETECTION OF PROTEOGLYCANS

[75] Inventor: Ralph Heimer, Philadelphia, Pa.

[73] Assignee: Thomas Jefferson University, Philadelphia, Pa.

[21] Appl. No.: 315,733

[22] Filed: Feb. 24, 1989

[51] Int. Cl.⁵ .................. G01N 33/53; G01N 33/543; C07K 17/00

[52] U.S. Cl. .......................... 435/7.1; 435/6; 435/7.92; 435/810; 436/501; 530/387.1; 530/387.5; 530/388.2

[58] Field of Search .................. 435/6, 810, 7.1, 7.92; 436/501; 536/27; 530/387, 387.1, 387.5, 388.2

[56] References Cited

U.S. PATENT DOCUMENTS 4,391,904 7/1983 Litman et al. ........................ 435/7
4,704,356 11/1987 Thonar .................................... 435/7
4,778,768 10/1988 Heinegard et al. ................. 436/501

OTHER PUBLICATIONS

Witter et al., "The Immunologic Detection and Characterization of Cartilage Proteoglycan Degradation Products In Synovial Fluids of Patients With Arthritis", Arthritis and Rheumatism, 30: 519–529 (1987).

Saxne, et al., Annals of the Rheumatic Diseases, 45:491–497 (1986).

Sampson, et al., Analytical Biochemistry, 151:304–308 (1985).

Heimer, et al., Analytical Biochemistry 165:448–455 (1987).

Primary Examiner—Margaret Moskowitz
Assistant Examiner—Ardin H. Marschel
Attorney, Agent, or Firm—Woodcock Washburn Kurtz Mackiewicz & Norris

[57] ABSTRACT

The invention discloses methods of detecting proteoglycans in synovial fluid and methods of monitoring treatment of diseases characterized by breakdown of proteoglycans into synovial fluid. A test sample of synovial fluid is contacted with antibodies specifically bindable with proteoglycan, the antibodies being bound to a solid support. Bound proteoglycan is then contacted with detectably labeled antibody specifically bindable with said proteoglycan and the detectable label is then detected.

13 Claims, No Drawings

IMMUMOASSAYS AND KIT FOR DETECTION OF PROTEOGLYCANS

FIELD OF THE INVENTION

The present invention relates to methods of detecting proteoglycans and glycosaminoglycans and methods of following the course of treatment of diseases characterized by breakdown of proteoglycans into synovial fluid.

BACKGROUND OF THE INVENTION

Proteoglycans are biological molecules composed of a protein core and covalently attached side chains of glycosaminoglycans. Proteoglycans and collagen are the primary components of articular cartilage found in knee and other joints. In articular cartilage, the side chain glycosaminoglycans are principally chondroitin sulfate and keratan sulfate. The proteoglycans in articular cartilage encompass classes containing variable amounts of both chondroitin sulfate and keratan sulfate. Proteoglycans are also found in skin, tendons, cornea, sclera and elsewhere in the body and vary in the type and number of glycosaminoglycan side chains and the molecular weight of the protein core. The types of proteoglycans and their distributions have been reviewed by Poole, Biochemical Journal, 236: 1-14, (1986).

In certain human degenerative joint diseases such as osteoarthritis and rheumatoid arthritis, excessive amounts of proteoglycans are lost from cartilage, eventually leading to cartilage degeneration and loss of joint function. Proteoglycans degraded from cartilage collect in the synovial fluid of the affected joints. In osteoarthritis a variety of proteoglycans containing chondroitin sulfate and keratan sulfate are found in synovial fluid. In gout, as well as in rheumatoid arthritis, synovial fluids contain proteoglycans which conform to other proteoglycan profiles.

Physicians treating patients presenting with swollen knee joints routinely extract synovial fluid from the swollen joint and analyze the contents of the synovial fluid to diagnose the cause of swelling. Routinely, the synovial fluid is subjected to a differential white cell count and to a search for the presence of urate or calcium pyrophosphate crystals. These tests are indicators of inflammation and the presence of crystals may pinpoint one of the causes of joint fluid effusion. Routinely also, synovial fluids are subjected to a test for viscosity to assess the state of hyaluronic acid and aggregates which it may form. Sometimes such a test is also connected to formation of a hyaluronic acid "mucin clot" which occurs when acetic acid is added to synovial fluid. Hyaluronic acid is produced by synovial lining cells and is responsible for the viscoelastic properties of synovial fluid. Its partial hydrolysis, resulting in lowered viscosity and negative "mucin clots", is one of the sequelae of inflammation. Thus routine tests of synovial fluid are directed mainly to assessing inflammatory states. This is clearly important to the patient's prognosis as prolonged joint inflammation results in cartilage destruction and attendant impairment of joint motion accompanied by pain. The most crippling of these inflammatory diseases is rheumatoid arthritis. Another form of joint destruction, probably unrelated to inflammation, is the underlying cause of osteoarthritis, a disease entity widespread among the elderly. Though there is an important need, there presently are no reliable tests which measure joint destruction. Because these degenerative diseases are chronic, patients with the diseases must be treated for an indefinite period of time. It thus becomes important to be able to monitor the effectiveness of treatments that adjustment in treatment can be made if necessary.

Existing methods of detecting proteoglycans and glycosaminoglycans are labor-intensive, time-consuming and some are not very sensitive to small quantities of proteoglycans. Faster, easier and more sensitive methods of detecting proteoglycans and glycosaminoglycans are needed.

Saxne, et al., Annals of the Rheumatic Diseases, 45: 91-497, (1986), detected proteoglycans with a competitive enzyme-linked immunosorbent assay (ELISA). Antibodies to human articular cartilage proteoglycan monomer were used to detect the presence of proteoglycans in synovial fluid of patient with swollen knee joints. Proteoglycan concentrations of less than 5 micrograms per milliliter were detected. Although this method is sensitive, it provides only limited information about the molecular form of the proteoglycan derived from cartilage. In addition, the assay is time-consuming, since the proteoglycans are enzymatically degraded for four hours before attaching to the solid phase and the synovial fluid test samples are enzymatically degraded for eight hours before use in the assay.

Witter et al., Arthritis and Rheumatism, 30: 519-529, (1987), detected proteoglycan degradation products in synovial fluids of patients with arthritis by separating the proteoglycans on an ion-exchange column followed by a gel permeation column and finally detected the proteoglycans in a competitive radioimmunoassay using antibodies to proteoglycans. This method is labor-intensive as well as time-consuming and unsuitable for the clinical laboratory.

Sampson et al., Analytical Biochemistry, 151: 304-308, (1985), detected glycosaminoglycans on cellulose acetate strips using $^{125}$I-labeled cytochrome c. This reagent was able to detect glycosaminoglycans at the level of 1 nanogram per 0.25 milliliters. These researchers found that $^{125}$I-cytochrome c was a more sensitive reagent for detecting glycosaminoglycans than Alcian Blue or Ponceau S which had a minimum sensitivity level of fifty nanograms per 0.25 milliliters.

Heimer et al., Analytical Biochemistry 165: 448-455 (1987) reported the detection of proteoglycans transblotted to positively charged nylon and detected with cationized $^{125}$I-cytochrome c. Using this method one nanogram of proteoglycan could be readily detected.

SUMMARY OF THE INVENTION

The invention provides methods of detecting proteoglycan in synovial fluid suspected of containing the proteoglycan. Test samples of proteoglycan are contacted with antibodies specifically bindable with proteoglycan that are bound to a solid support. Bound proteoglycan is then contacted with a substance bindable with proteoglycan; and the substance is then detected.

The invention also provides methods for detecting joint destruction in human degenerative diseases. In these diseases proteoglycans are degraded from cartilage and appear in the synovial fluid of the affected joint. The presence of increased amounts of certain types of proteoglycan in the synovial fluid, as compared to normal synovial fluid, is thus indicative of joint destruction.

There appear to be differences among degenerative diseases in the composition and quantity of proteoglycans in synovial fluid. By selecting the antibodies used in the methods of the invention to reflect the type of proteoglycan or proteoglycan side chain present in the synovial fluid when a particular degenerative disease is present, it may be possible to use the methods of the invention to diagnose, or differentiate between different degenerative diseases.

The methods of the invention are also useful for following the course of treatment of a degenerative disease to prevent or contain joint destruction. The methods of the invention are performed at intervals selected by the physician or patient. The initial determination will serve as a baseline or reference point for future determinations. A decrease in the amount of proteoglycan in synovial fluid detected by the methods of the invention would indicate a lessening of joint destruction, and hence the efficacy of treatment; whereas an increased amount would indicate a worsening of joint destruction.

DETAILED DESCRIPTION OF THE INVENTION

The methods of the invention are preferably performed by binding antibodies specific for a glycosaminoglycan side chain or non-glycosaminoglycan component of proteoglycans to a solid support, and dipping the solid support into test samples of synovial fluid, and reagent solutions. Excess amounts of test samples and reagents are removed between the steps of the methods of the invention by dipping the solid support into buffer solution or rinsing with a buffer solution.

Suitable antibodies for use in the methods of the invention may be polyclonal or monoclonal. Monoclonal antibodies to keratan sulfate, chondroitin sulfate, other glycosaminoglycans and non-glycosaminoglycan parts of proteoglycan molecules, such as the core proteins, are commercially available through ICN ImmunoBiologicals, Lisle, Illinois or other sources. Polyclonal antibodies to glycosaminoglycans and other parts of the proteoglycan molecule produced by conventional techniques can also be used.

Antibodies specific for proteoglycan are bound to a solid support. Suitable solid supports include nitrocellulose and plastic materials to which antibodies can adhere. The solid support may be of any shape suitable for dipping into a container, such as a rectangular, circular or square shape. Antibodies are preferably bound to at least a portion of the solid support, with some portion of the solid support remaining free of antibodies to form a handle for grasping the solid support. Unreacted sites on the solid support are preferably blocked with a suitable protein, such as albumin.

The solid support with antibodies bound thereon is dipped into a test sample of synovial fluid taken from a patient suspected, or already diagnosed as having a disease wherein proteoglycans are degraded from cartilage and collect in synovial fluid of a joint. It may be necessary to dilute or otherwise prepare the test sample for use in the immunoassays of the invention. If the sample is to be diluted before use, it is diluted with a suitable diluent to give at least a twenty to one dilution of the synovial fluid test sample. Suitable diluents include physiological saline solutions and other physiologically acceptable solutions. The actual dilution will depend on such factors a the total amount of synovial fluid taken from the patient and the amount of proteoglycan expected to be in the sample.

The solid support is left in the test sample for a length of time sufficient for binding of at least a portion of proteoglycans present in the test sample to antibodies on the solid support. The solid support is then removed from the test sample. Excess test sample is then removed by rinsing or dipping the solid support into a suitable buffer such as phosphate buffered saline.

Next, proteoglycan bound to antibodies on the solid support are contacted with detectably labeled antibody specifically bindable to proteoglycans and the detectable label is then detected. Suitable antibodies include antibodies specific for either glycosaminoglycans or non-glycosaminoglycan constituents of proteoglycans, as described for antibodies bound to the solid support, as well as antibodies to human IgG. The detectable label is preferably an enzyme capable of causing a color change in a substrate solution. Suitable enzymes are horse radish peroxidase and alkaline phosphatase. These enzymes are commercially available from sources such as Sigma Chemical Co., St. Louis, Mo. Suitable substrates for these enzymes include hydrogen peroxide, o-phenylenedianime, p-nitrophenyl phosphate and 3,3',5,5' tetramethylbenzidine. These substrates are available from commercial sources such as Sigma Chemical Co., St. Louis, Mo. The enzymes and substrates are used according to manufacturers instructions or standard texts on immunoassays. Determination of enzyme activity can be made using colorimetric measurement, spectrophotometry at an appropriate wavelength for the substrate used or by visual inspection.

Using the methods of the invention, one or more types of proteoglycans can be detected using the same test sample. For example, proteoglycans containing both keratan sulfate and chondroitin sulfate can be distinguished in the following way. Antibody to either chondroitin sulfate or keratan sulfate is impregnated onto separate strips of nitocellulose. After exposure to the synovial fluid, the keratan sulfate impregnated and chondroitin sulfate strips is then placed into a container containing either detectably labeled anti-keratan sulfate antibody or detectably labeled anti-chondroitin sulfate antibody. This will produce "sandwiches" having chondroitin sulfate antibody or keratan antibody on both sides or "sandwiches" having chondroitin sulfate-keratan sulfate or keratan sulfate-chondroitin sulfate on either side of the proteoglycan in the middle. Proteoglycans containing both chondroitin sulfate and keratan sulfate will be distinguished by the heterogeneous "sandwiches" from proteoglycans containing predominantly keratan sulfate or chondroitin sulfate.

To quantitate the proteoglycans present in the synovial fluid test sample, it is preferable to use a method of detecting the detectable label that gives quantitative results, such as horseradish peroxidase. The result from the test sample can then be compared to results of the methods of the invention performed with known quantities of proteoglycans to determine the amount of proteoglycan in the test sample.

The invention further provides kits for the detection of proteoglycans in synovial fluid. The kits comprise antibodies specific for a selected glycosaminoglycan or non-glycosaminoglycan component of peoteoglycans bound to a solid support; a reagent comprising antibodies specific for proteoglycan having a detectable label bound thereon; and at least one reagent comprising means for detecting for the detectable label. The kits may also comprise standard charts for comparing with results from test samples. These standard charts would contain color charts of known amounts of proteoglycans for comparison and quantitation of the amounts of proteoglycans present in the test sample. The kits may further comprise additional containers of suitable buffers for rinsing the solid support between steps. The reagent comprising means for detecting the detectable label would be coordinated with the detectable label to form a detection system. Some suitable detection systems may require more than one reagent for detection of the detectable label, in which case the additional reagents would also be supplied in the kits. Examples of suitable detectable labels and detection systems are those described herein. Suitable solid supports are nitrocellulose and other solid supports known in the art.

A kit for the detection of proteoglycans in synovial fluid would comprise, for example, antibodies to chondroitin sulfate bound to a nitrocellulose strip; a reagent comprising antibodies specific for chondroitin sulfate having horseradish peroxidase bound thereon, at least one reagent comprising substrate for the horseradish peroxidase. The reagents of the kit are designed to be used in sequence to achieve a color change if chondroitin sulfate-containing proteoglycan is present in the test sample.

For convenience in using the kits away from a laboratory, such as in a physician's office, a chromogenic detection system, such as a system employing horseradish peroxidase is preferred. With chromogenic detection systems such as these, the antibodies can be visualized by eye without the aid of any equipment.

If it is desired to quantitate the amount of antibody present and thus the amount of proteoglycan present when performing the methods of the invention, a detection system employing horseradish peroxidase is preferred.

EXAMPLE

Separate nitrocellulose strips impregnated with antibody to keratan sulfate or to chondroitin sulfate are prepared. The strips are "blocked" with chicken egg albumin and then dipped into tubes containing 1 ml of phosphate buffered saline with a 0.05 percent Tween-20 content to which 50 $\mu$l of suitably diluted (at least on to twenty) test synovial fluid solution has been added. Each strip is shaken for 10 seconds and removed to another tube containing 10 ml of phosphate buffered saline. The strip is dried on filter paper and placed into a tube containing 1 ml phosphate buffered saline and 0.05 percent Tween which also contains either 10 microliter of mouse monoclonal antibody to keratan sulfate or chondroitin sulfate conjugated to horseradish peroxidase. After shaking the tube for 10 seconds, the strip is washed, as before, in a tube containing 10 ml of phosphate buffered saline, and then dried on filter paper. The amount of horseradish peroxidase conjugated mouse monoclonal antibody sticking to the nitrocellulose strip is determined through the development of a blue color remaining fixed to the nitrocellulose strip. The developing solution is in a tube containing equal parts of two separately furnished solutions, called substrates: A: prepared as 0.045 percent hydrogen peroxide in 0.1M, pH 4.7 citrate buffer and B: prepared as 0.06 percent 3,3′, 5,5′ tetramethylbenzidine dihydrochloride-dihydrate in 0.1M, pH 2.7 citrate buffer with a 40 percent glycerol content. Development of color is allowed to proceed for two minutes upon which the nitrocellulose strip is washed with tap water and dried on filter paper. The intensity of the blue color developed is an index of the amount of proteoglycan present in the synovial fluid that had been tested. A color chart will be provided to the user, in which color intensity can be matched with quantity of proteoglycan epitope.

Four different proteoglycan values can be generated. This is based on having strips impregnated with antibody to either keratan sulfate or chondroitin sulfate. After exposure to the synovial fluid, each strip can then be placed into a tube containing either the horseradish peroxidase conjugated anti-keratan sulfate or anti-chondroitin sulfate antibody, i.e. CS-CS, CS-KS, KS-KS, and KS-CS. Reactivity with the horseradish peroxidase labeled antibodies will be dependent upon the availability of free epitopes of proteoglycans bound in the first step by either keratan sulfate or chondroitin sulfate epitopes. Using all four possible combinations of antibody should give a more complete profile of proteoglycan than using a lesser number of combinations.

What is claimed is:

1. A method of detecting proteoglycans in synovial fluid suspected of containing said proteoglycans, comprising the steps of:
    (a) providing first and second solid supports having antibody specific for a first glycosaminoglycan component of proteoglycan bound thereon, and third and fourth solid supports having antibody specific for a second glycosaminoglycan component of proteoglycan bound thereon;
    (b) contacting said synovial fluid with antibody specific for a first glycosaminoglycan component of proteoglycan on said first solid support under conditions which allow binding of proteoglycan in said synovial fluid to said antibody specific for said first glycosaminoglycan component of proteoglycan;
    (c) contacting bound proteoglycan on said first solid support with a detectably labeled antibody specific for said first glycosaminoglycan component of proteoglycan;
    (d) detecting said detectable label on said antibody specific for said first glycosaminoglycan component of proteoglycan;
    (e) contacting said synovial fluid with antibody for a first glycosaminoglycan component of proteoglycan on said second solid support under conditions which allow binding of proteoglycan in said synovial fluid to said antibody specific for said first glycosaminoglycan component of proteoglycan;
    (f) contacting bound proteoglycan on said second solid support with detectably labeled antibody specific for a second glycosaminoglycan component of proteoglycan;
    (g) detecting said detectable label on said antibody specific for said second glycosaminoglycan component of proteoglycan;
    (h) contacting said synovial fluid with antibody specific for said second glycosaminoglycan component of proteoglycan on said third solid support under conditions which allow binding of proteoglycan in said synovial fluid to said antibody specific for said second glycosaminoglycan component of proteoglycan;
    (i) contacting bound proteoglycan on said third solid support with a detectably labeled antibody specific for said first glycosaminoglycan component of proteoglycan;
    (j) detecting said detectable label on said antibody specific for said first glycosaminoglycan component of proteoglycan;

(k) contacting said synovial fluid with antibody for a second glycosaminoglycan component of proteoglycan on said fourth solid support under conditions which allow binding of proteoglycan in said synovial fluid to said antibody specific for said second glycosaminoglycan component of proteoglycan;

(l) contacting bound proteoglycan on said fourth solid support with a detectably labeled antibody specific of said second glycosaminoglycan component of proteoglycan;

(m) detecting said detectable label on said antibody specific for said second glycosaminoglycan component of proteoglycan; and (n) comparing the results obtained in detecting steps d, g, j and m for said first, second, third, and fourth solid supports whereby the presence of detectable label on said first, second, third and fourth solid supports indicates the presence in said synovial fluid of proteoglycan containing both said first glycosaminoglycan component and said second glycosaminoglycan component; the presence of detectable label on said first solid support along with the absence of detectable label on said second, third and fourth solid supports indicates the presence in said synovial fluid of proteoglycan containing said first glycosaminoglycan component; and the presence of detectable able on said fourth solid support along with the absence of detectable label on said first, second, and third solid supports indicates the presence in said synovial fluid of proteoglycan containing said second glycosaminoglycan component, thus distinguishing between proteoglycan containing said first and said second glycosaminoglycan component and proteoglycan containing said first glycosaminoglycan component or said second glycosaminoglycan component.

2. A method of monitoring treatment of diseases characterized by the breakdown of proteoglycans into synovial fluid comprising the following steps:

(a) providing a sample of a body fluid suspected of containing proteoglycan form a mammal undergoing treatment of a disease characterized by the breakdown of proteoglycans into synovial fluid;

(b) treating said sample according to the method of claim 1 to identify proteoglycan in said sample; and (c) repeating steps (a) and (b) at pre-selected times during treatment to thereby monitor said treatment.

3. A method of detecting joint destruction in humans comprising the following steps:

(a) providing a sample of synovial fluid form said joint suspected of containing proteoglycans;

(b) providing first and second solid supports having antibody specific for a first glycosaminoglycan component of proteoglycan bound thereon, and third and fourth solid supports having antibody specific for a second glycosaminoglycan component of proteoglycan bound thereon;

(c) contacting said synovial fluid with antibody specific for a first glycosaminoglycan component of proteoglycan on said first solid support under conditions which allow binding of proteoglycan in said synovial fluid to said antibody specific for said first glycosaminoglycan component of proteoglycan;

(d) contacting bound proteoglycan on said first solid support with a detectably labeled antibody specific for said first glycosaminoglycan component of proteoglycan;

(e) detecting said detectable label on said antibody specific for said first glycosaminoglycan component of proteoglycan;

(f) contacting said synovial fluid with antibody for a first glycosaminoglycan component of proteoglycan on said second solid support under conditions which allow binding of proteoglycan in said synovial fluid to said antibody specific for said first glycosaminoglycan component of proteoglycan;

(g) contacting bound proteoglycan on said second solid support with a detectably labeled antibody specific for a second glycosaminoglycan component of proteoglycan;

(h) detecting said detectable label on said antibody specific for said second glycosaminoglycan component of proteoglycan;

(i) contacting said synovial fluid with antibody specific for said second glycosaminoglycan component of proteoglycan on said third solid support under conditions which allow binding of proteoglycan in said synovial fluid to said antibody specific for said second glycosaminoglycan component of proteoglycan;

(j) contacting bound proteoglycan on said third solid support with a detectably labeled antibody specific for said first glycosaminoglycan component of proteoglycan;

(k) detecting said detectable label on said antibody specific for said first glycosaminoglycan component of proteoglycan;

(l) contacting said synovial fluid with antibody for a second glycosaminoglycan component of proteoglycan on said fourth solid support under conditions which allow binding of proteoglycan in said synovial fluid to said antibody specific for said second glycosaminoglycan component of proteoglycan;

(m) contacting bound proteoglycan on said fourth solid support with a detectably labeled antibody specific for said second glycosaminoglycan component of proteoglycan;

(n) detecting said detectable able on said antibody specific for said second glycosaminoglycan component of proteoglycan; and (o) comparing the results obtained in detecting steps e, h, k and n for said first, second, third, and fourth solid supports whereby the presence of detectable able on said first, second, third, or fourth solid supports indicates the presence in said synovial fluid of proteoglycan and an increased concentration of proteoglycan in comparison with the concentration of proteoglycan in a sample of normal synovial fluid indicates the presence in said synovial fluid of proteoglycans characteristic of joint destruction and whereby the presence of an increased concentration of detectable label on said first, second, third and fourth solid supports indicates the presence in said synovial fluid of proteoglycan containing both said first and second glycosaminoglycan components; the presence of an increased concentration of detectable label on said first solid support in comparison with the concentration of detectable label on said second, third and fourth solid supports indicates the presence in said synovial fluid of proteoglycan containing said first glycosaminoglycan component; and the presence of an increased concentration of detectable able on said fourth solid support in comparison with the concentration of detectable label on said first, second, and third solid supports indicates the presence in said synovial fluid of proteoglycan containing said second glycosaminoglycan component, thus distinguishing between proteoglycan containing both said first and said second glycosaminoglycan components and proteoglycan containing said first glycosaminoglycan component or said second glycosaminoglycan component.

4. The method of claim 1 wherein said detectable label is an enzyme.

5. The method of claim 4 wherein said enzyme is horse-radish peroxidase.

6. The method of claim 1 wherein said solid support is nitrocellulose.

7. The method of claim 2 wherein said detectable label is an enzyme.

8. The method of claim 7 wherein said enzyme is horse-radish peroxidase.

9. The method of claim 2 wherein said solid support is nitrocellulose.

10. The method of claim 3 wherein said detectable label is an enzyme.

11. The method of claim 10 wherein said enzyme is horse-radish peroxidase.

12. The method of claim 3 wherein said solid support is nitrocellulose.

13. A kit for detecting proteoglycans in body fluids comprising:
(a) antibody specific for a first glycosaminoglycan component of proteoglycan bound to solid supports;
(b) antibody specific of a second glycosaminoglycan component of proteoglycan bound to solid supports;
(c) a reagent comprising antibody specific for said first glycosaminoglycan component of proteoglycan having detectable label bound thereon;
(d) a reagent comprising antibody specific for said second glycosaminoglycan component of proteoglycan having detectable able bound thereon;
(e) at least one reagent comprising means for detecting said detectable label; and
(f) a proteoglycan standard chart for determination of the amount of proteoglycan present in said sample of body fluid.

* * * * *

UNITED STATES PATENT AND TRADEMARK OFFICE
CERTIFICATE OF CORRECTION

PATENT NO. : 5,185,245

DATED : February 9, 1993

INVENTOR(S) : Ralph Heimer

It is certified that error appears in the above-identified patent and that said Letters Patent is hereby corrected as shown below:

Column 7, line 53, Claim 3, change "form" to --from--.

Signed and Sealed this

Thirtieth Day of November, 1993

BRUCE LEHMAN

*Attest:*

*Attesting Officer*   *Commissioner of Patents and Trademarks*